(12) United States Patent
Cheng

(10) Patent No.: US 10,058,255 B2
(45) Date of Patent: Aug. 28, 2018

(54) METHOD OF DETERMINING STIFFNESS INDEX OF AN ARTERIAL NETWORK AND SYSTEM THEREOF

(71) Applicant: Hong Kong Applied Science and Technology Research Institute Co. Ltd., Shatin, New Territories (HK)

(72) Inventor: Chi Kit Cheng, New Territories (HK)

(73) Assignee: Hong Kong Applied Science and Technology Research Institute Co. Ltd., Hong Kong (CN)

( * ) Notice: Subject to any disclaimer, the term of this patent is extended or adjusted under 35 U.S.C. 154(b) by 1101 days.

(21) Appl. No.: 14/289,649

(22) Filed: May 29, 2014

(65) Prior Publication Data

US 2015/0342471 A1     Dec. 3, 2015

(51) Int. Cl.
*A61B 5/0255* (2006.01)
*A61B 5/021* (2006.01)
*A61B 5/00* (2006.01)

(52) U.S. Cl.
CPC ........ *A61B 5/0255* (2013.01); *A61B 5/02116* (2013.01); *A61B 5/7246* (2013.01); *A61B 5/7282* (2013.01)

(58) Field of Classification Search
CPC . A61B 5/02007; A61B 5/022; A61B 5/02116; A61B 5/7246; A61B 5/7282; A61B 5/0255
See application file for complete search history.

(56) References Cited

U.S. PATENT DOCUMENTS

| | | | |
|---|---|---|---|
| 6,712,768 B2 | 3/2004 | Ogura et al. | |
| 7,074,193 B2 | 7/2006 | Satoh et al. | |
| 7,291,113 B2 | 11/2007 | Satoh et al. | |
| 2006/0173366 A1 | 8/2006 | Hasegawa | |
| 2009/0264775 A1 | 10/2009 | Wu | |
| 2010/0081945 A1* | 4/2010 | Sethi | A61B 5/02007 600/485 |
| 2010/0198088 A1 | 8/2010 | Ortenberg et al. | |

(Continued)

FOREIGN PATENT DOCUMENTS

| | | |
|---|---|---|
| CN | 1432339 | 7/2003 |
| CN | 202458330 | 10/2012 |

(Continued)

OTHER PUBLICATIONS

Huotari, Matti, et al. "Photoplethysmography and its detailed pulse waveform analysis for arterial stiffness." Journal of Structural Mechanics 44.4 (2011): 345-362.

*Primary Examiner* — Christian Jang
*Assistant Examiner* — Michael Catina
(74) *Attorney, Agent, or Firm* — Eagle IP Limited; Jacqueline C. Lui

(57) ABSTRACT

A method of determining stiffness index of an arterial network is disclosed. The method comprises the steps of: obtaining a pulse waveform related to the arterial network; estimating a source pulse based on at least one predetermined feature of the pulse waveform; determining a plurality of characteristics of the pulse waveform based on a relationship between the pulse waveform and the source pulse; and calculating the stiffness index of the arterial network based on the plurality of characteristics of the pulse waveform. An arterial stiffness index measuring device employing the above methodology is also disclosed therein.

5 Claims, 6 Drawing Sheets

(56) References Cited

U.S. PATENT DOCUMENTS

2013/0324859 A1* 12/2013 Park .................. A61B 5/02007
                                                            600/479
2014/0135632 A1   5/2014 Sharrock et al.
2015/0057554 A1*  2/2015 Watson .............. A61B 5/02125
                                                            600/485

FOREIGN PATENT DOCUMENTS

| | | |
|---|---|---|
| CN | 103070678 | 5/2013 |
| CN | 103690152 A | 4/2014 |
| CN | 103705224 | 4/2014 |
| CN | 104146692 A | 11/2014 |
| GB | 2356251 | 5/2001 |
| WO | 2014022906 A1 | 2/2014 |

* cited by examiner

METHOD OF DETERMINING STIFFNESS INDEX OF AN ARTERIAL NETWORK AND SYSTEM THEREOF

FIELD OF INVENTION

The present invention relates to a method of determining the stiffness index of an arterial network and in particular to a method of determining the arterial stiffness index from a radial pulse waveform.

BACKGROUND OF INVENTION

When our hearts beat, pulse waves, also known as aortic pulses, are generated and propagated along the arterial network of the cardiovascular system. When these pulse waves reach sites with impedance mismatch such as vessel bifurcations and site with changes in vessel radius, wave reflections will be produced. These wave reflections could be captured at various measurement sites. For example, the wave reflections measured at the wrist of a human body is known as radial pulse waveform. Previous researches have proposed using the ratio of late systolic peak to early systolic peak of the radial pulse waveform as the arterial stiffness index. Nonetheless, an accurate location of early systolic peak and late systolic peak is not a trivial task. First of all, the early systolic peak and late systolic peak may be too close to each other. Secondly, the amplitude of the late systolic component is too small compared to that of the early systolic component. These two scenarios increase the difficulties of an accurate separation of early systolic component and the late systolic component. Furthermore, depending on the choice of measurement site and the subject of interest, the radial pulse waveform measured may be too noisy and weak for post-processing.

Different methodologies have been proposed to deal with the aforesaid limitations, for instance curve fitting method and waveform classification based on $n^{th}$ derivative of the radial pulse waveform. Nonetheless, these methodologies suffer from different inherit limitations. For curve fitting method, it usually takes more than 100 iterations in order to accurately decompose a radial pulse waveform. Such high computation demand limits the practical application of such technologies. For derivative-based classification, it is well known that derivative operation would amplify the high frequency noises. As such, the classification is very sensitive to noise and prone to error.

SUMMARY OF INVENTION

In the light of the foregoing background, it is an object of the present invention to an alternative method of determining the arterial stiffness index from a radial pulse waveform which is low computational demand and accurate.

In one aspect, the present invention is a method of determining a stiffness index of an arterial network comprising the steps of: obtaining a pulse waveform related to the arterial network; estimating a source pulse based on at least one predetermined feature of the pulse waveform; determining a plurality of characteristics of the pulse waveform based on a relationship between the pulse waveform and the source pulse; and calculating the stiffness index of the arterial network based on the plurality of characteristics of the pulse waveform.

In one embodiment, the step of estimating the source pulse further comprises the steps of: identifying the inflexion point of the first rising phase of the pulse waveform; identifying the predetermined feature by calculating the slope and the value of the inflexion point; and constructing the source pulse based on the slope and the value of the inflexion point.

In one embodiment, the method further comprises the steps of: decomposing the pulse waveform into at least two components based on the relationship between the pulse waveform and the source pulse; determining a first characteristic of the pulse waveform based on a first component of the pulse waveform; and determining a second characteristic of the pulse waveform based on a second component of the pulse waveform.

In one embodiment, the method further comprises a step of calculating an impulse response of the arterial network, thereby obtaining the relationship between the pulse waveform and the source pulse. In yet another embodiment, the method further comprises the steps of: segmenting the impulse response into at least two segments; convoluting a first segment of the impulse response with the source pulse thereby obtaining the first component of the pulse waveform; and convoluting a second segment of the impulse response with the source pulse thereby obtaining the second component of the pulse waveform.

In another embodiment, the method further comprises the steps of: identifying the peak of the first component of the pulse waveform, thereby obtaining the first characteristic of the pulse waveform; identifying the peak of the second component of the pulse waveform, thereby obtaining the second characteristic of the pulse waveform; and calculating a ratio between the peak of the first component of the pulse waveform and the peak of the second component of the pulse waveform, thereby obtaining the stiffness index of the arterial network.

According to another aspect of the present invention, a system of determining stiffness index of an arterial network is disclosed. The system comprises: a pressure sensor configured to obtain a pulse waveform related to the arterial network; a microprocessor coupled to the pressure sensor; and a non-transitory computer-readable storage medium coupled to the microprocessor. The non-transitory computer-readable storage medium is encoded with computer-readable instructions for causing the microprocessor to execute the following steps: obtaining the pulse waveform; estimating a source pulse based on a predetermined feature of the pulse waveform; determining a first characteristic and a second characteristic of the pulse waveform based on a relationship between the pulse waveform and the source pulse; and calculating the stiffness index of the arterial network based on the first characteristic and the second characteristic of the pulse waveform.

In one embodiment, the system further comprises: a cuff configured to surround a predefined portion of a subject wherein the pressure sensor is disposed within the cuff; and a pump coupled to the cuff and the microprocessor. The non-transitory computer-readable storage medium is further encoded with computer-readable instructions for causing the microprocessor to activate the pump to inflate the cuff to fitly surround the predefined portion of the subject, thereby obtaining the pulse waveform.

The present invention provides a less computational demanding method of determining arterial stiffness index based on a radial pulse waveform. Furthermore, this method is less sensitive to noise and less prone to error when comparing with derivative-based classification methodologies. The method of the present invention also improves accuracy.

BRIEF DESCRIPTION OF THE DRAWINGS

For a more complete understanding of the present invention, reference is made to the following detailed description and accompanying drawings, in which.

DETAILED DESCRIPTION OF THE PREFERRED EMBODIMENTS

As used herein and in the claims, "comprising" means including the following elements but not excluding others.

As used herein and in the claims, "couple" or "connect" refers to electrical coupling or connection either directly or indirectly via one or more electrical means unless otherwise stated.

Figure 1:
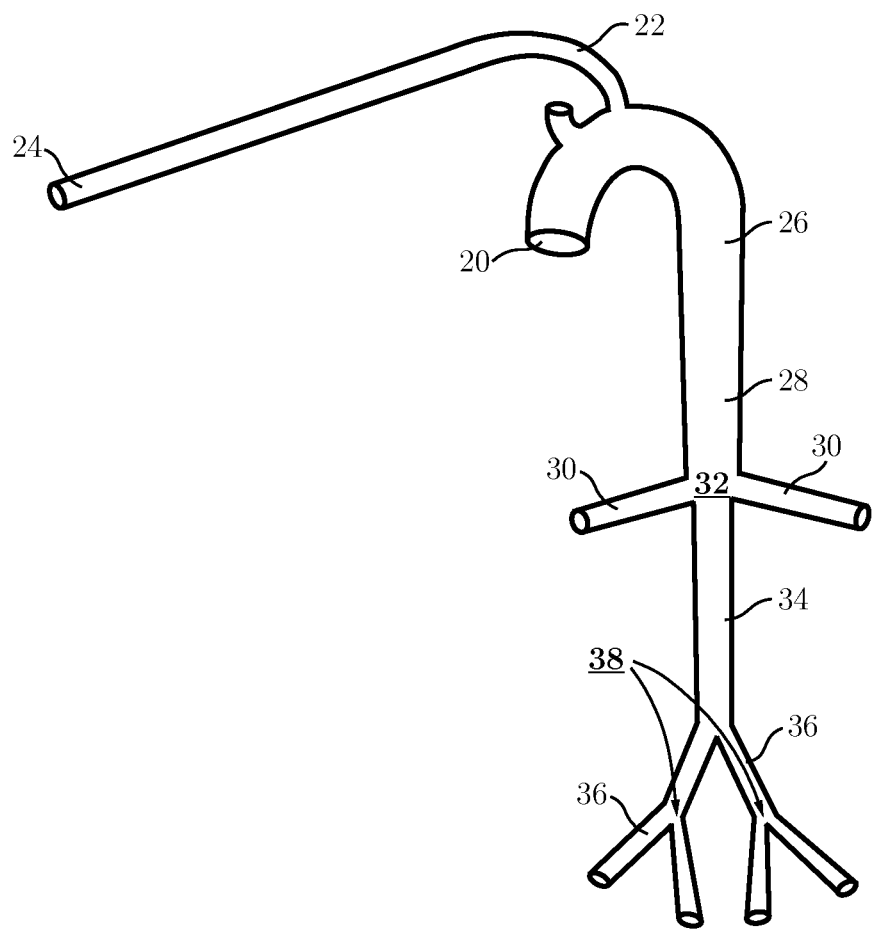
FIG. 1 shows a simplified arterial network model of a human being according to one specific embodiment of the present invention.
Figure 2:
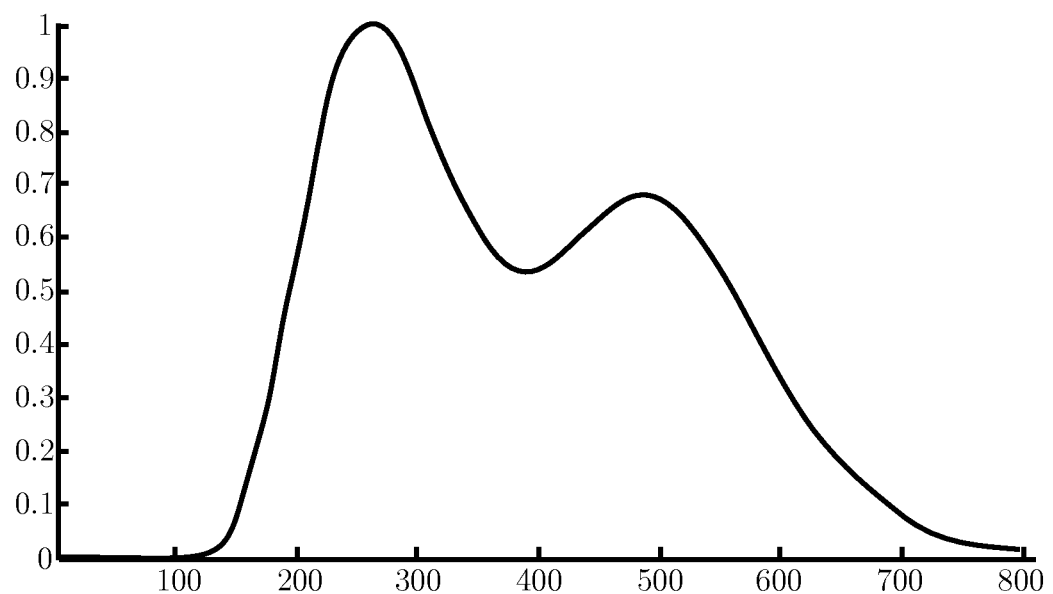
FIG. 2 shows a typical radial pulse measured at the wrist of a human subject.

Referring to FIG. 1, a simplified arterial network model of a human being according to one embodiment of the present invention is shown. The pulse waveform generated by the heart (not shown), also known as aortic pulse, first propagates along the aortic arch 20. When it reached the bifurcation between aortic arch 20 and brachial artery 22, part of the aortic pulse will propagate to the radial artery 24 via the brachial artery 22 and eventually measured by a sensor (not shown) placed near the radial artery 24. On the other hand, the rest of the aortic pulse continues to propagate down to the thoracic aorta 26 and upper abdominal aorta 28 until it reaches the first reflection site 32, which is the bifurcation between upper abdominal aorta 28 and renal arteries 30. At the first reflection site 32, part of the aortic pulse will be reflected back and reaches the radial artery 24 via upper abdominal aorta 28, thoracic aorta 26 and brachial artery 22; whereas the remaining aortic pulse will continue to propagate down to the lower abdominal aorta 34 until it reaches the second reflection site 38 which is the bifurcation between lower abdominal aorta 34 and iliac arteries 36. At the second reflection site 38, part of the aortic pulse will be reflected back to the radial artery 24 via lower abdominal aorta 34, upper abdominal aorta 28, thoracic aorta 26 and brachial artery 22; whereas the remaining aortic pulse will continue to propagate down to the lower limbs of the human being. It should be noted that the pulse waveform measured by the sensor near the radial artery 24, also known as radial pulse, includes three components: (1) originated from the heart and propagate directly to the radial artery 24; (2) reflected from the first reflection site 32; and (3) reflected from the second reflection site 38. FIG. 2 shows a typical radial pulse measured at the wrist of a human subject.

Mathematically, the aforesaid simplified arterial network model, which governs the relationship between the aortic pulse and the radial pulse, can be expressed by the equation (1).

$$y(t)=x(t)\otimes h(t)=x(t)\otimes h_1(t)+x(t)\otimes h_2(t)+x(t)\otimes h_3(t) \quad (1)$$

where y(t) is the radial pulse measured by the sensor, x(t) is the aortic pulse and h(t) is the impulse response of the arterial network. The impulse response h(t) further includes: (1) $h_1(t)$ which is the impulse response of the path from the aortic arch 20 directly to the radial artery 24 via the brachial artery 22; (2) $h_2(t)$ which is the impulse response of the path from aortic arch 20 to the first reflection site 32 and back to the radial artery 24 and (3) $h_3(t)$ which is the impulse response of the path from aortic arch 20 to the second reflection site 38 and back to the radial artery 24.

The method, according to one embodiment of the present invention, first constructs an approximated aortic pulse x(t) in the form of a Gaussian function based on the inflexion point of the first rising phase of the radial pulse y(t). The inflexion point is characterized by its value B and the slope S. These two parameters are calculated by setting the second derivative of the radial pulse y"(t) to zero and substituting the corresponding result back to the radial pulse y(t) and the first derivative of the radial pulse y'(t) respectively.

The general form of a Gaussian function is expressed in the equation (2). The first derivative and the second derivative of the Gaussian function are shown in equation (3) and equation (4) respectively.

$$x(t) = Ae^{-\frac{t^2}{2b^2}} \quad (2)$$

where A is the amplitude and b related to the width of the Gaussian function $$x'(t) = -\frac{At}{b^2}e^{-\frac{t^2}{2b^2}} \quad (3)$$

$$x''(t) = -\frac{A(t^2-b^2)}{b^4}e^{-\frac{t^2}{2b^2}} \quad (4)$$

In order to locate the inflexion point of a Gaussian function, the second derivative of the Gaussian function as shown in equation (4) is set to zero which yield the solution of t=−b or t=b. As such, the value and the slope at the inflexion point of the Gaussian function, which are the same as that of the radial pulse, are determined by equation (5) and equation (6) respectively. Based on the intermediate results of equation (5) and equation (6), the parameters A and b can be determined.

$$B = x(-b) = Ae^{-\frac{1}{2}} \Rightarrow A = Be^{\frac{1}{2}} \quad (5)$$

$$S = x'(-b) = \frac{A}{b}e^{-\frac{1}{2}} = \frac{B}{b} \Rightarrow b = \frac{B}{S} \quad (6)$$

By substituting the parameters A and b as shown in equation (5) and equation (6) back into equation (2), the approximated aortic pulse can be expressed as equation (7).

Figure 3:
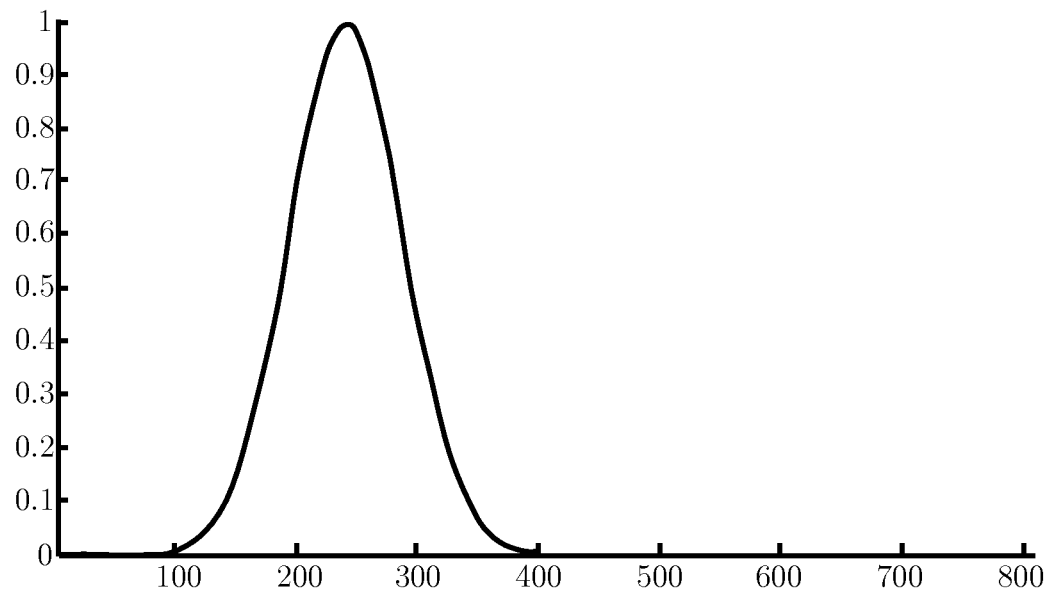
FIG. 3 shows an approximated aortic pulse according to one specific embodiment of the present invention.

The approximated aortic pulse x(t) obtained using equation (7) based on the radial pulse y(t) as shown in FIG. 2 is shown in FIG. 3.

$$x = Be^{-\frac{S^2 t^2}{2B^2} + \frac{1}{2}} \quad (7)$$

where B is the value of the inflexion point of the first rising phase of the radial pulse y(t) and S is the slope of the same inflexion point.

After obtaining the approximated aortic pulse x(t), the impulse response of the arterial network can be deconvoluted from the arterial network model as shown in equation (1). In matrix form, the arterial network model as shown in equation (1) can be rewritten as equation (8).

$$y = Xh \quad (8)$$

where $$X = \begin{pmatrix} x(0) & 0 & 0 & \cdots & 0 & 0 \\ x(1) & x(0) & 0 & \cdots & 0 & 0 \\ x(2) & x(1) & x(0) & \cdots & 0 & 0 \\ \vdots & \vdots & \vdots & \ddots & \vdots & \vdots \\ x(n-1) & x(n-2) & x(n-3) & \cdots & x(0) & 0 \\ x(n) & x(n-1) & x(n-2) & \cdots & x(1) & x(0) \end{pmatrix}$$

Figure 4:
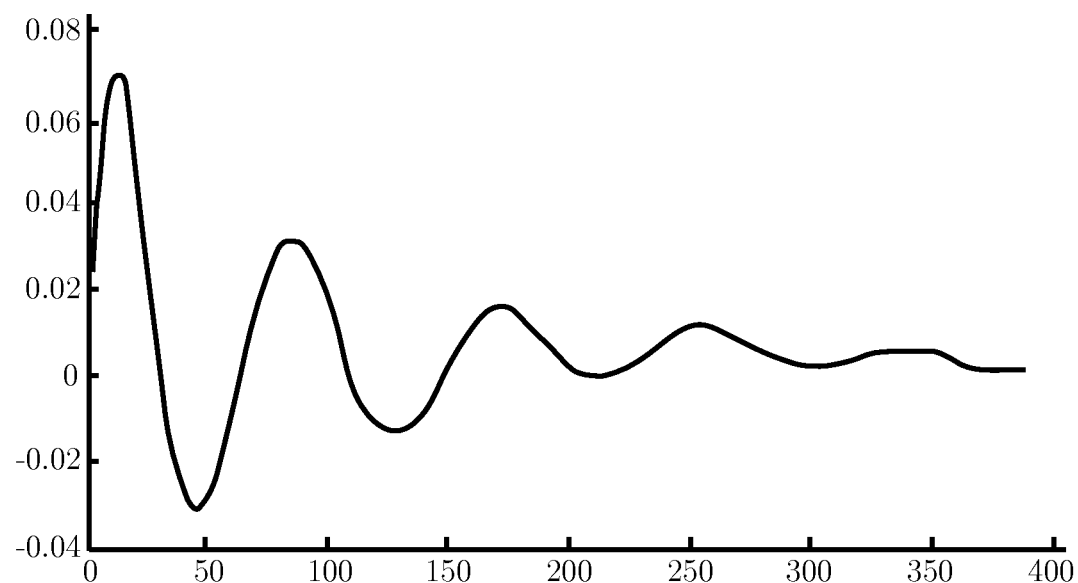
FIG. 4 shows a reconstructed impulse response based on the radial pulse as shown in FIG. 2 and the approximated aortic pulse as shown in FIG. 3 according to one specific embodiment of the present invention.

However, it is impossible to find h directly as X is not invertible. According to one embodiment of the present invention, least square method as shown in equation (9) is used to obtain the impulse response h. The reconstructed impulse response obtained thereof based on the radial pulse as shown in FIG. 2 and the approximated aortic pulse as shown in FIG. 3 is shown in FIG. 4.

$$h \approx (X^T X + \lambda I)^{-1} X^T y \quad (9)$$

where $X^T$ is the transpose of X and $\lambda$ is a small number >0, for instance 0.1.

Figure 5:
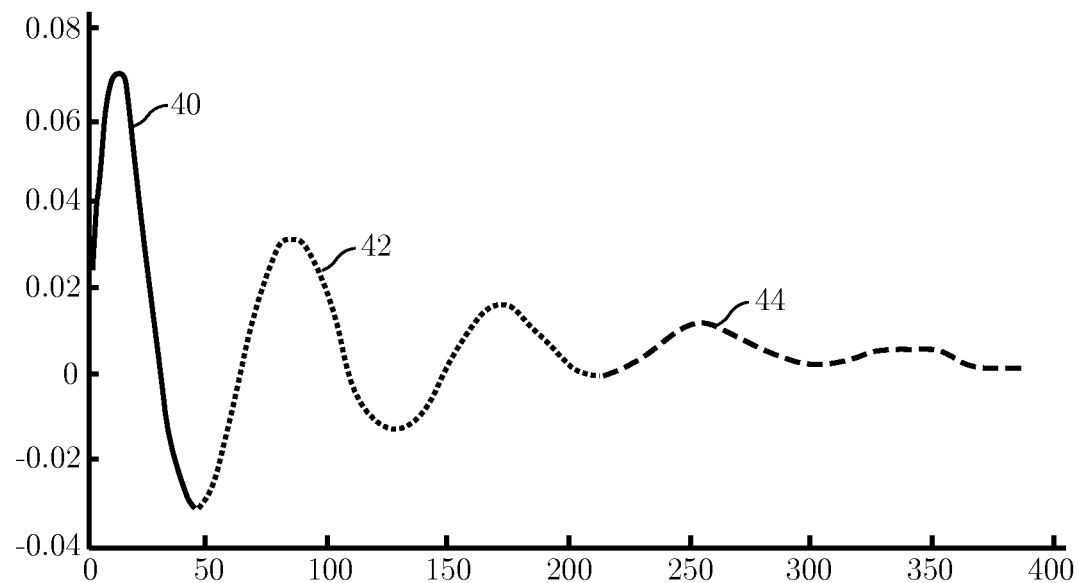
FIG. 5 shows the three segments segmented from the reconstructed impulse response as shown in FIG. 4 according to one specific embodiment of the present invention.

After obtaining the reconstructed impulse response h of the arterial network, segmentation is employed to identify the three segments: (1) originated from the heart; (2) reflected from the first reflection site 32; and (3) reflected from the second reflection site 38 of the impulse response h. In one embodiment of the present invention, the segmentation is conducted based on the anatomy of a human being. The travelling time of a pulse from the heart to the thoracic aorta 26, the upper abdominal aorta 28, the lower abdominal aorta 34 and iliac arteries 36 are approximately 36 ms, 14 ms, 27 ms and 34 ms respectively. Therefore the time delay between the peak of the first component of the radial pulse and the peak of the second component of the radial pulse is 100 ms (i.e. the back and forth travelling time of the thoracic aorta 26 plus the back and forth travelling time of the upper abdominal aorta 28 is 2×(36 ms 14 ms)=100 ms); whereas the time delay between the peak of the first component of the radial pulse and the peak of the third component of the radial pulse is 222 ms (i.e. the back and forth travelling time of the thoracic aorta 26 plus the back and forth travelling time of the upper abdominal aorta 28 plus the back and forth travelling time of lower abdominal aorta 34 plus the back and forth travelling time of iliac arteries 36 is 2×(36 ms 14 ms+27 ms+34 ms)=222 ms). Based on the aforesaid time delays, the reconstructed impulse response h can be segmented in time domain into three segments, i.e. $h_1(t)$, $h_2(t)$ and $h_3(t)$. The end point of each segment is defined as the local minimum point of the impulse response h with a predefined time interval. The time interval is based on the aforesaid time delays plus certain tolerance. In this embodiment, the end points of the first segment $h_1(t)$ and the second segment $h_2(t)$ are defined as the local minimum point of the impulse response h within 50-150 ms and 170-270 ms respectively. The corresponding segmentation result of the impulse response as indicated in FIG. 4 is shown in FIG. 5, which shows the first segment 40 (from the start to 50 ms), the second segment 42 (from 50 ms to 210 ms) and the third segment 44 (beyond 210 ms). It should be noticed that, the impulse response $h_1(t)$ is assumed to die down beyond the first segment 40 (i.e. $h_1(t)=0$ for t>100 ms); the impulse response $h_2(t)$ is zero in the first segment 40 and third segment 44 (i.e. $h_2(t)=0$ for 100 ms≤t<444 ms) and the impulse response $h_3(t)$ is zero in the first segment 40 and second segment 42 (i.e. $h_3(t)=0$ for t≤444 ms).

Figure 6:
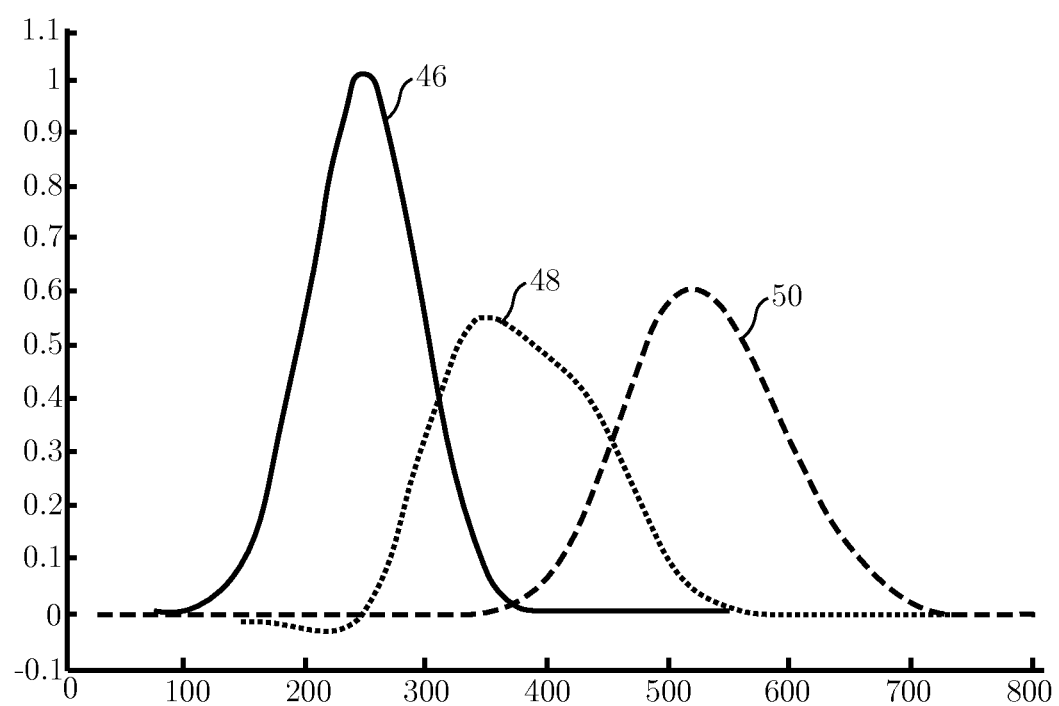
FIG. 6 shows the three components decomposed from the radial pulse as shown in FIG. 2 according to one specific embodiment of the present invention.

With the first segment 40, the second segment 42 and the third segment 44 of the impulse response, the radial pulse can then be decomposed into three components based on equation (1), wherein the first component, the second component and the third component are $x(t) \otimes h_1(t)$, $x(t) \otimes h_2(t)$ and $x(t) \otimes h_3(t)$ respectively. The corresponding decomposed components of the radial pulse as indicated in FIG. 2 is shown in FIG. 6, which shows the first component 46, second component 48 and third component 50. The peak of the first component 46, second component 48 and third component 50 are known as early systolic peak, late systolic peak and diastolic peak respectively. The arterial stiffness index is calculated as the ratio of the late systolic peak to the early systolic peak, i.e. the ratio of the peak of the second component 48 and that of the first component 46. The arterial stiffness index is positively correlated with various diseases, for instance coronary artery diseases, myocardial infarction, heart failure, hypertension, stroke, diabetes mellitus, end-stage renal disease, hypercholesterolemia and inflammation.

Figure 7:
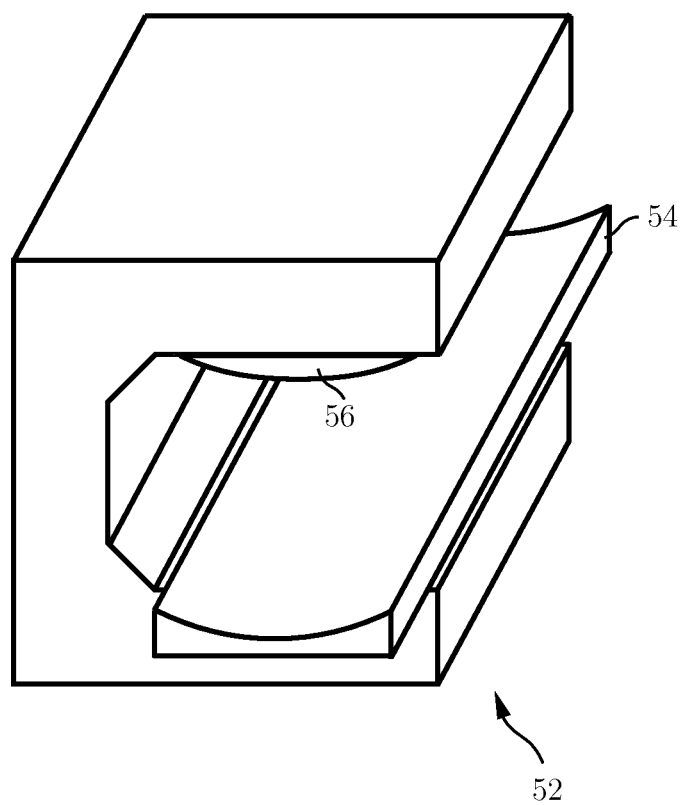
FIG. 7 is a schematic view of an arterial stiffness index measuring device according to one specific embodiment of the present invention.
Figure 8:
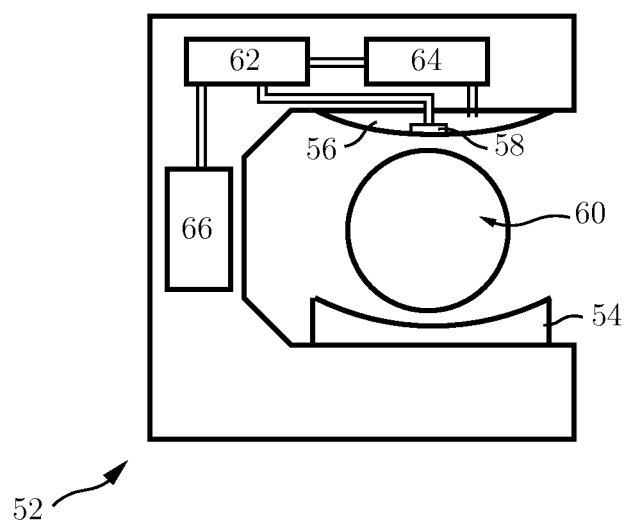
FIG. 8 is a schematic configuration diagram of an arterial stiffness index measuring device according to one specific embodiment of the present invention.

Referring now to FIG. 7, an arterial stiffness index measuring device 52 according to one embodiment of the present invention is shown. The arterial stiffness index measuring device 52 is of a C-shape. At the bottom side of the cavity surrounded by the C-shape structure is an arm holder 54. The arm holder 54 has a convex upper surface configured to accept a human arm during operation. On the other hand, an inflatable cuff 56 is disposed at the upper side of the same cavity. As shown in FIG. 8, there is a pressure sensor 58 disposed at the lower surface, which is the surface that would be in contact with the wrist 60 of the human subject during operation, of the cuff 56 thereby allowing the pressure sensor 58 to capture the radial pulse of human subject and transfer the same to the microprocessor 62. The cuff 56 is also in connection with a pump 64, which is controlled by the microprocessor 62. The microprocessor 62 is further coupled to a non-transitory computer-readable storage medium 66. The storage medium 66 is encoded with computer-readable instructions for causing the microprocessor 62 to execute the steps of the method of determining the stiffness index of an arterial network as stated above.

During operation of the arterial stiffness index measuring device 52, a person first puts his arm, with his palm facing upward, into the cavity of the arterial stiffness index measuring device 52 and rests on the arm holder 54. The microprocessor 62 will then activate the pump 64 to inflate the cuff 56. The pressure sensor 58 disposed with the cuff 56 is pushed against the radial artery of the person. The inflation process stops when a predefined pressure is achieved with the cuff 56. Subsequently, the pressure sensor 58 starts recording the radial pulse waveform and transfers the same to the microprocessor 62. The storage medium 66 is encoded with computer-readable instructions for causing microprocessor 62 to calculate the arterial stiffness index based on the method as stated above.

The exemplary embodiments of the present invention are thus fully described. Although the description referred to particular embodiments and realizations, it will be clear to one skilled in the art that the present invention may be practiced with variation of these specific details. Hence this invention should not be construed as limited to the embodiments set forth herein.

For instance, although wrist is chosen as the measurement of the pulse waveform, it should be obvious to one skilled in the art to notice that other measurement sites, for instance neck and thigh, could also be adopted in order to measure the corresponding pulse waveform. It should also be notice that, depending on the measurement sites, different arterial model will be adopted accordingly.

Regarding the approximation of the aortic pulse, it is approximated to be a Gaussian function in the above-mentioned embodiments. Nonetheless, other bell shape functions, for instance log-normal and Rayleigh, could also be used to approximate the aortic pulse. Furthermore, the value and slope of the inflexion point of the first rising phase of the radial pulse are used as the basis in the approximation step. It should be clear to one skilled in the art that other methods can also be used. Moreover, other features of the first rising phase of the pulse waveform can be used in the approximation step, for instance the slope and values of any two arbitrary points within the first rising phase of the pulse waveform.

Propagation time delays between components of the radial pulse are used in the segmentation of impulse response. However, the segmentation can be done by associating the impulse response segments with particular analytical functions and segmenting the impulse response accordingly. Other methodologies, for instance curve fitting and principal component analysis, could also be adopted. The travelling time of a pulse from the heart to the thoracic aorta 26, the upper abdominal aorta 28, the lower abdominal aorta 34 and iliac arteries 36 used can be within 10% of the above mentioned travelling time.

What is claimed:

1. An electronic device that determines a stiffness index of an arterial network of a person, comprising:
   a pressure sensor that obtains a pulse waveform related to said arterial network of the person;
   a microprocessor that determines the stiffness index of the arterial network based on the pulse waveform, wherein the microprocessor
   obtains the pulse waveform from the pressor sensor;
   estimates an aortic pulse generated by a heart of the person based on at least one feature of said pulse waveform, wherein the aortic pulse x is represented by:

$$x = Be^{-\frac{s^2 t^2}{2B^2} + \frac{1}{2}}$$

where B is a value of an inflexion point at a rising phase of the pulse waveform, S is a slope of the inflexion point, and t is time;
locates a first peak and a second peak from the pulse waveform based on a relationship between said pulse waveform and said aortic pulse represented by:

$$y(t) = x(t) \otimes h(t)$$

where y(t) is the pulse waveform measured by the pressure sensor, x(t) is the aortic pulse and h(t) is an impulse response of the arterial network of the person; and
calculates said stiffness index of said arterial network based on the first peak and the second peak of said pulse waveform.

2. The electronic device of claim 1 further comprises:
a cuff configured to surround a predefined portion of the person, wherein said pressure sensor is disposed within said cuff;
a pump connected to said cuff and said microprocessor;
wherein the microprocessor of the device activates said pump to inflate said cuff to fitly surround said predefined portion of the person, such that the pressure sensor obtains said pulse waveform after a predetermined pressure between the predefined portion of the person and the cuff is achieved.

3. The electronic device of claim 1, wherein said microprocessor further
decomposes said pulse waveform into a first component and a second component based on said relationship between said pulse waveform and said aortic pulse;
determines a first peak value of said pulse waveform from the first component of said pulse waveform;
determines a second peak value of said pulse waveform from the second component of said pulse waveform; and
calculates the stiffness index of the arterial network of the person by calculating a ratio between the first peak value and the second peak value.

4. The electronic device of claim 1, wherein said microprocessor
deconvolutes said pulse waveform by said aortic pulse to obtain the impulse response of said arterial network; and
decomposes said pulse waveform into at least two components based on said impulse response of said arterial network.

5. The electronic device of claim 1, wherein said microprocessor further
segments said impulse response into at least two segments based on an anatomy of said arterial network of the person;
convolutes a first segment of said impulse response with said aortic pulse to obtain a first component of said pulse waveform;
convolutes a second segment of said impulse response with said aortic pulse to obtain a second component of said pulse waveform; and
calculates the stiffness index of the arterial network of the person based on a peak value of the first component of the pulse waveform and a peak value of the second component of the pulse waveform.

* * * * *